(12) United States Patent
Hanson

(10) Patent No.: US 6,387,118 B1
(45) Date of Patent: May 14, 2002

(54) NON-CRIMPED STENT DELIVERY SYSTEM

(75) Inventor: Scott M. Hanson, Savage, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/553,034

(22) Filed: Apr. 20, 2000

(51) Int. Cl.[7] .................................. A61F 2/06
(52) U.S. Cl. ...................................... 623/1.11
(58) Field of Search .................... 623/1, 1.11–1.13, 623/1.28, 1.23, 12, 1.36; 606/108, 194, 195, 191, 200, 198, 192; 604/104, 96

(56) References Cited

U.S. PATENT DOCUMENTS

| | | | | |
|---|---|---|---|---|
| 4,950,227 A | * | 8/1990 | Savin et al. | 623/1.11 |
| 5,108,416 A | * | 4/1992 | Ryan et al. | 623/1.11 |
| 5,158,548 A | | 10/1992 | Lau et al. | 604/96 |
| 5,403,341 A | | 4/1995 | Solar | 606/198 |
| 5,453,090 A | | 9/1995 | Martinez | 604/53 |
| 5,534,007 A | * | 7/1996 | St. Germain et al. | 623/1.11 |
| 5,628,755 A | | 5/1997 | Heller et al. | 606/108 |
| 5,643,278 A | * | 7/1997 | Wijay | 623/1.11 |
| 5,709,703 A | | 1/1998 | Lukic et al. | 606/198 |
| 5,788,707 A | | 8/1998 | Del Toro et al. | 606/108 |
| 5,951,569 A | * | 9/1999 | Tuckey et al. | 623/1.11 |
| 5,980,530 A | * | 11/1999 | Willard et al. | 623/1.11 |
| 6,068,634 A | * | 5/2000 | Cornelius et al. | 623/1.11 |
| 6,113,608 A | * | 9/2000 | Monroe et al. | 623/1.11 |
| 6,174,327 B1 | * | 1/2001 | Mertens et al. | 623/1.11 |
| 6,183,505 B1 | * | 2/2001 | Mohn, Jr. et al. | 623/1.11 |
| 6,206,888 B1 | * | 3/2001 | Bicek et al. | 623/1.11 |
| 6,221,097 B1 | * | 4/2001 | Wang et al. | 623/1.11 |

FOREIGN PATENT DOCUMENTS

EP 0 990 427 5/2000

* cited by examiner

Primary Examiner—Henry J. Recia
Assistant Examiner—Tan-Uyen T. Ho
(74) Attorney, Agent, or Firm—Vidas, Arrett & Steinkraus, P.A.

(57) ABSTRACT

A stent delivery system which includes a single or a pair of stent retaining sleeves having a ribbed configuration. The ribbed configuration providing the sleeves with reduced columnar strength and an improved radial strength characteristics. The sleeves of the present stent delivery system further providing a recoil action in opposite longitudinal directions when the stent is being expanded. The recoil assists in fully retracting the sleeves from the stent.

14 Claims, 2 Drawing Sheets

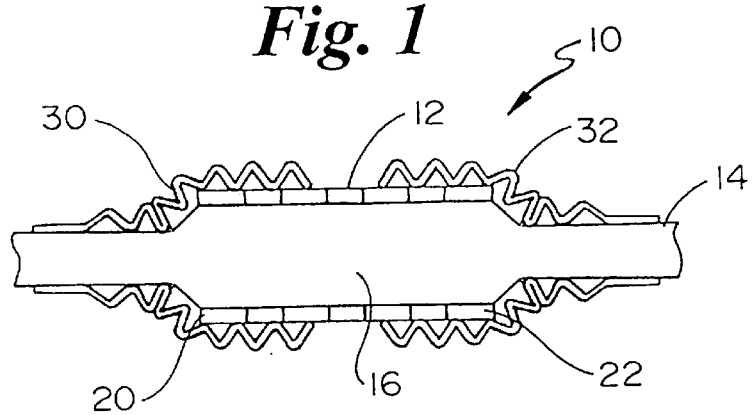
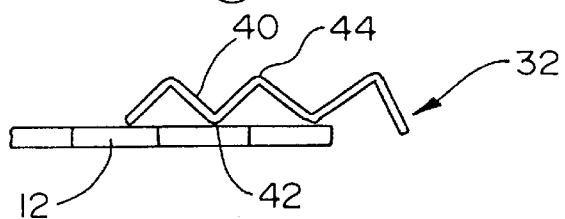
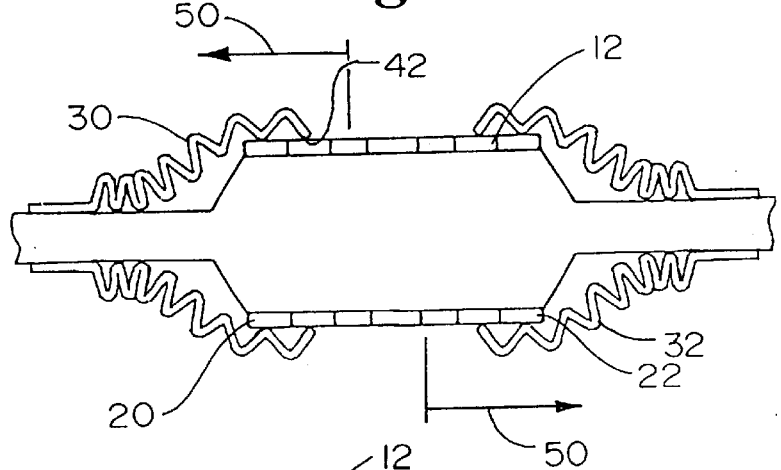
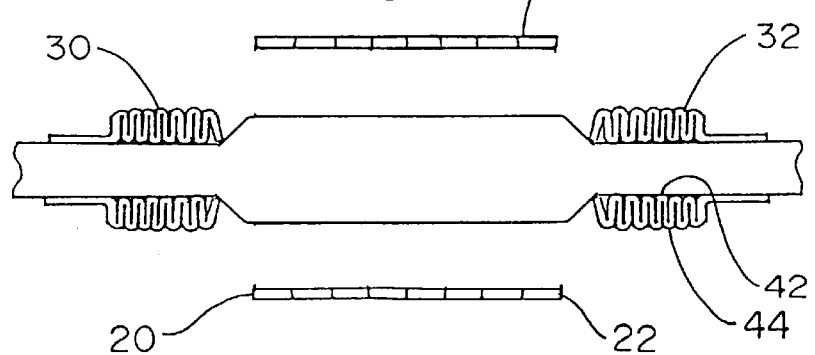

NON-CRIMPED STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

It is well understood that stents which are not properly secured or retained to the catheter may slip and either be lost or be deployed in the wrong location or partially deployed. Traditionally, in order to provide proper securement of the stent on the catheter the stent is crimped to a predetermined area of the catheter.

In the past, crimping has been done by hand or by a crimping apparatus, often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

The present invention avoids these problems by providing ribbed stent retaining sleeves which are capable of securing a stent to the catheter without the need to crimp the stent into place. The ribbed sleeves may be utilized with nearly any type of stent. Both self-expanding and inflation expandable stents are well known and widely available in a variety of designs and configurations. Self-expanding stents must be maintained under a contained sheath or sleeve(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter without translocating proximally or distally and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Another invention which may be relevant to the present invention is disclosed in a concurrently filed and commonly assigned U.S. patent application entitled: U.S. Application entitled FULLY SHEATHED EXPANDABLE STENT DELIVERY SYSTEM, designated by U.S. application Ser. No. 09/552807.

All of the references contained herein, including the co-pending Application listed above, are respectively incorporated in their entirety herein by reference.

BRIEF SUMMARY OF THE INVENTION

This invention provides an improvement over the prior art, by providing a stent delivery system which includes one or more stent retaining sleeves having a ribbed configuration. The ribbed configuration provides the one or more sleeves with a reduced columnar strength and improved radial strength characteristics. The ribbed sleeves of the present invention are capable of retaining and immobilizing a non-crimped stent on the catheter surface by completely covering all or only a portion of the stent, the sleeves are readily retracted from off of the stent to provide for safe and effective stent release.

The sleeve or sleeves have a ribbed configuration. The ribbed configuration provides a plurality of alternating raised and lowered pleats, with the lowered pleats contacting the stent. The sleeve or sleeves may be composed of an elastic polymer, a non-elastic polymer or a combination thereof.

The reduced columnar strength of the sleeves is at least in part a consequence of having only the downward pleats of the sleeves, rather than the entire sleeve, frictionally engage the stent surface. The reduced columnar strength provided by this arrangement allows the sleeves to be retracted from the stent without the need to apply lubrication to the stent/sleeve surfaces.

The ribbed configuration of the sleeves further provides a spring or recoil action to the sleeves which is triggered when the stent is expanded. The recoil action of each sleeve is directed in longitudinally opposing directions and assists in actively retracting the sleeves off of the stent in the appropriate direction. The combination of the recoil action and the reduced columnar strength of the sleeves, allows the sleeves to be pulled completely off of the stent with improved effectiveness.

As may be understood from viewing the various figures included herein, the unique physical characteristics of the present sleeves, most notably the recoil action, provides the present invention with the capacity to include sleeves which may be fitted over increased areas of the stent as opposed to merely the stent edges or ends as provided for in many prior stent delivery systems. By providing sleeves which may cover the entire stent the present invention helps to ensure that the stent is completely immobilized on the stent surface. In addition, the potentially increased coverage provided by the sleeves reduces the potential for accidental or premature stent delivery and may help to protect the stent from damage prior to and during stent delivery.

The ribbed configuration of the sleeves also provides the sleeves with radial strength characteristics sufficient to provide an interference fit between each of the sleeves and the stent. The interference fit retains the sleeves in a desired position and in a reduced configuration until the recoil action is triggered by the expansion of the stent. The radial strength characteristics of the ribbed sleeves are such that even during the retraction of the sleeves the interference fit is maintained, thus providing a uniform and consistent retraction of the sleeves while also ensuring that the retracted sleeves do not interfere with the safe removal of the catheter from the vessel subsequent to stent delivery.

BRIEF DESCRIPTION OF THE SEVERAL VIEWS OF THE DRAWINGS

A detailed description of the invention is hereafter described with specific reference being made to the drawings in which:

FIG. 1 is a side view of the stent delivery system showing the ribbed sleeves and the stent in the unexpanded position;

FIG. 2 is a close-up view of a sleeve showing the alternating raised and lowered pleats;

FIG. 3 is a side view of the stent delivery system of FIG. 1 shown during the expansion of the stent;

FIG. 4 is a side view of the stent delivery system of FIG. 1 shown after the stent is fully expanded;

DETAILED DESCRIPTION OF THE INVENTION

Figure 5:
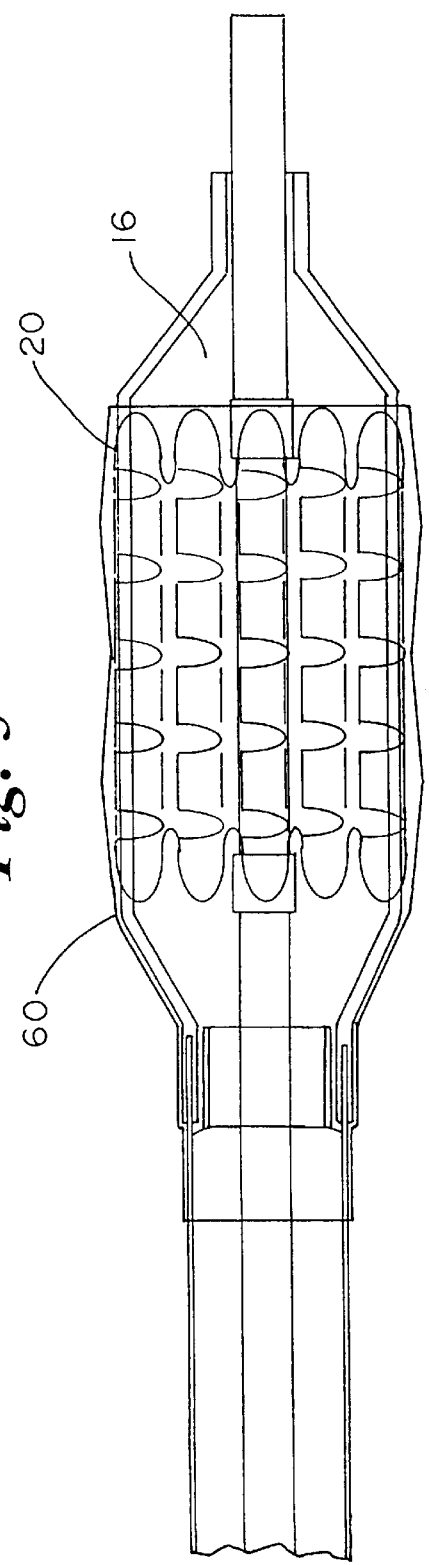
FIG. 5 is a side view of an alternative embodiment of the inventive stent delivery system.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows a first embodiment of a stent delivery system, indicated generally at 10, which includes a stent 12 mounted upon a stent delivery catheter 14. FIG. 1 shows the stent delivery system prior to stent delivery. A pair of sleeves: proximal sleeve 30 and distal sleeve 32 are employed to retain the stent ends 20 and 22 on an inflatable portion 16 of the delivery catheter 14 prior to stent delivery.

Stent 12 is placed on the delivery catheter 14 by placing the stent on a stent mandrel and reducing the stent to a diameter sufficient for mounting the stent on the catheter. Preferably the stent 12 is reduced directly onto the inflatable portion 16. As previously indicated, the present invention provides for stent retaining sleeves 30 and 32 which have sufficient radial strength to retain a reduced, but non-crimped stent on the delivery catheter.

As may be best seen in FIG. 2 the sleeves 30 and 32 respectively have ribbed portions 40 which may be characterized as being made up of a plurality of folds or pleats which have been pressed into the sleeve material. The pleats are comprised of alternating lower pleats 42 and raised pleats 44. The sleeves 30 and 32 are preferably constructed from polyurethane such as Techothane® 1055D produced by Thermedics Inc. located in Woburn, Mass. Other materials may be alternatively or additionally used, such as: elastic polymers, non-elastic polymers and any combinations thereof. The pleats 42 and 44 are formed by swelling an extruded tube and then shrinking the tube over a mandrel with the desired pleat configuration. The tube is then heat set on the mandrel. Finally, the heat seated pleated sleeve is expanded off of the mandrel.

As shown in FIGS. 1 and 3, regardless of the condition of the stent, whether it is in the unexpanded state or it is being expanded for delivery, only the lower pleats 42 are in contact with the stent surface 12. By providing sleeves which contact the stent surface in such a limited manner, the sleeves 30 and 32 will have a reduced frictional engagement against the stent ends 20 and 22. This reduced frictional engagement translates functionally to a reduced columnar strength in the sleeves 30 and 32. As a result, the sleeves may be retracted from the stent with no need to have a supplemental lubricant added between the stent and sleeves.

In addition to the reduced columnar strength provided by the ribbed configuration of the sleeves 30 and 32, the ribbed configuration assists in ready retraction of the sleeves from the stent by providing the sleeves with a recoil action. As may be seen in FIG. 2, the pleats 42 and 44 provide the sleeves 30 and 32 with a zig-zag pattern much like that of a spring. This pattern of alternating pleats provides each of the sleeves with a tension force in longitudinally opposing directions.

As seen in FIG. 3, the direction of the tension force and resulting recoil action of the sleeves 30 and 32 is illustrated by arrows 50 and 52. As indicated by arrow 50, the tension force of proximal sleeve 30 provides a recoil action to the sleeve 30 in the proximal direction. As indicated by arrow 52, the tension force of distal sleeve 32 provides a recoil action to the sleeve 32 in the distal direction. The recoil action of the sleeves 30 and 32 is triggered when the stent begins to expand from the unexpanded position to the expanded position. The combination of the reduced columnar strength of the sleeves and their respective recoil actions allows the sleeves to be readily and completely retracted from off of the stent when the stent is expanded. Preferably, the pleats 44 and 42 will retract when the inflatable portion 16 is expanded under a pressure of approximately 6 atmospheres. The pressure may vary in alternative embodiments.

The present invention provides an additional advantage over prior stent retaining sleeve(s). The unique configuration of the present stent retaining sleeve(s) allows the sleeves to be retained on the catheter 14 and stent 12 without requiring the reduced diameter portion 70 and 72 of the sleeves 30 and 32 to be bonded to the catheter 14.

In the present embodiment shown and described in FIGS. 1–4, the retraction of the sleeves 30 and 32 off of the stent 12 occurs simultaneously. In other embodiments where it may be desirable to have one end of the stent freed sooner than the other end, the individual sleeves may be configured to have different retraction rates by altering the individual sleeve's composition and/or pleat arrangement.

Figure 6:
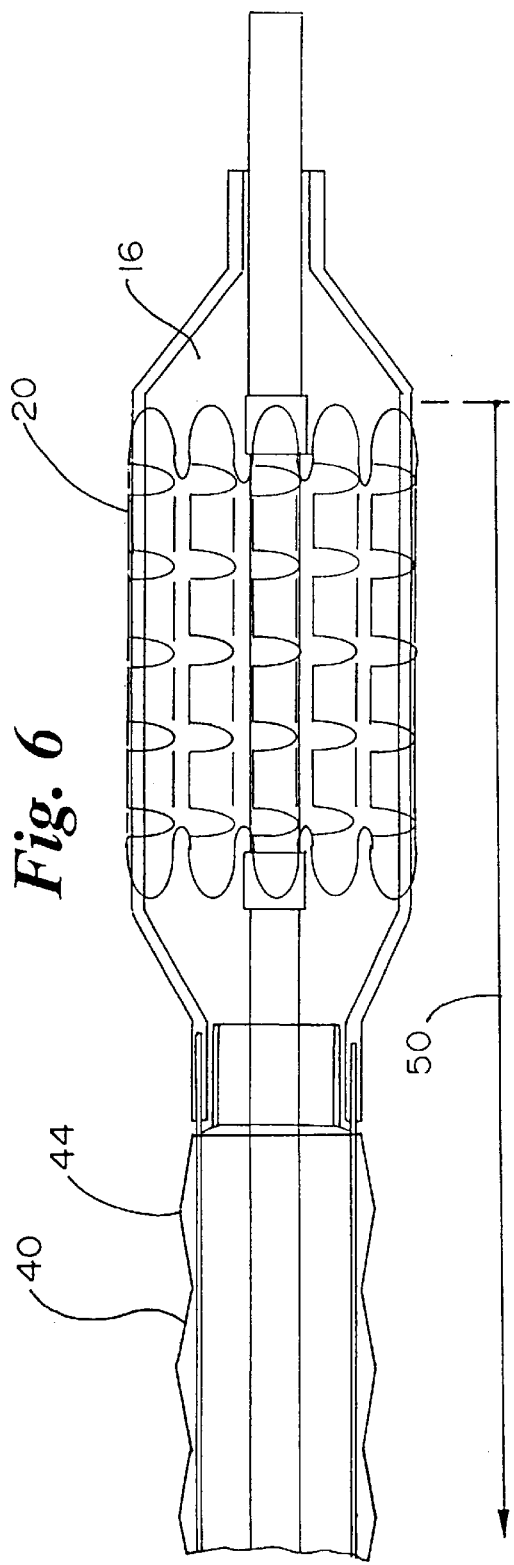
FIG. 6 is a side view of the alternative embodiment shown in FIG. 5 wherein the sleeve has been retracted proximally from the stent delivery catheter.

As may be seen in an alternative embodiment shown in FIGS. 5 and 6, the stent 12 may be equipped with a single sleeve 60. The single sleeve 60 may preferably be positioned on the proximal end of the catheter 14 as shown in FIG. 5. Alternatively, the sleeve may be positioned over the distal end of the catheter. The ease of retraction provided by the pleats 42 and 44 makes it possible to overlap the entire stent 12 or only a portion thereof, while still allowing the sleeve 60 to be fully retracted when the stent 12 is expanded, such as may be seen in FIGS. 6. When the inflatable portion 16 and the stent 12 are expanded, the sleeve 60 is fully withdrawn from the stent 12 in the appropriate direction such as indicated by arrow 50 in FIG. 6.

Whether the catheter includes a single pleated sleeve overlapping only the proximal or distal end of the stent, or the catheter is equipped with a pleated sleeve on both ends of the stent, the pleats 42 and 44 provide for sufficiently reduced columnar strength to fully retract off of the stent for safe and effective stent delivery. As may best be seen in FIG. 6 the sleeve 60 (or sleeves 30 and 32 such as shown in FIGS. 1–4) may be configured to only retract off of the stent, or the sleeve or sleeves may be configured to retract as well as fold back on themselves. Such a folding action provides for a reduced profile of the catheter during retraction.

Turning to FIG. 4 the stent 12 is shown in the expanded, delivered state. In order to properly deliver stent 12, the sleeves 30 and 32 must be fully retracted off of stent ends 20 and 22. As previously stated prior to expansion of stent 12, the sleeves 30 and 32 provide an inward radial force sufficient to immobilize the stent on catheter 14 and to retain the stent in the unexpanded state, such as may be seen in FIG. 1. The radial force provided by the sleeves 30 and 32 is maintained even after the sleeves are fully removed from stent 12. As a result the sleeves 30 and 32 will tend to collapse upon themselves and maintain the relatively low profile of catheter 14 despite the added relative height of the compacted pleats 42, 44.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
   a stent delivery catheter, the stent delivery catheter having a stent mounting region, the stent mounting region having an inflatable portion;
   a stent disposed about the stent mounting region, the stent having an unexpanded position and an expanded position;
   at least one stent retaining sleeve disposed about at least a portion of the stent in the unexpanded position, at least a portion of the at least one stent retaining sleeve having a contractible pleated configuration.

2. The stent delivery system of claim 1 wherein the stent further comprises a pair of ends, the at least one stent retaining sleeve having a stent retaining portion and a catheter portion, the stent retaining portion of the at least one stent retaining sleeve disposed about at least an end of the stent in the unexpanded position, the catheter portion of the at least one stent retaining sleeve disposed about a portion of the stent delivery catheter substantially adjacent to the respective end of the stent.

3. The stent delivery catheter of claim 2 wherein at least the stent retaining portion of the at least one stent retaining sleeve having a ribbed configuration.

4. The stent delivery catheter of claim 2 wherein at least the catheter portion of the at least one stent retaining sleeve having an interference fit about the portion of the stent delivery catheter substantially adjacent to the respective end of the stent.

5. The stent delivery device of claim 1 wherein the ribbed configuration is defined by a plurality of alternating raised and lowered pleats placed at least one sleeve.

6. The stent delivery system of claim 1 where in the at least one stent retaining sleeve further comprises a proximal stent retaining sleeve and a distal stent retaining sleeve.

7. The stent delivery system of claim 6 wherein the ribbed configuration of the proximal and distal sleeves provides each sleeve with a tension force in the opposite longitudinal direction of the other sleeve.

8. The stent delivery system of claim 7 wherein the tension force of each sleeve acts as a recoil action when the stent is expanded from the unexpanded to the expanded state.

9. The stent delivery system of claim 8 wherein the recoil action is defined as a retraction of the sleeves off of a respective end of the stent during stent expansion.

10. The stent delivery system of claim 9 wherein the retraction of each sleeve occurs simultaneously.

11. The stent delivery device of claim 1 wherein the at least one stent retaining sleeve is constructed from at least one member of the group essentially consisting of polyurethane, elastic polymers, non-elastic polymers and any combinations thereof.

12. The stent delivery device of claim 11 wherein the polyurethane is TECHOTHANE.

13. The stent delivery device of claim 1 wherein the stent is further characterized as being pre-reduced.

14. The stent delivery device of claim 1 wherein the stent is further characterized as having not been crimped.

* * * * *